US009976951B2

(12) United States Patent
Ryo et al.

(10) Patent No.: US 9,976,951 B2
(45) Date of Patent: May 22, 2018

(54) PROTECTIVE FILM DETECTING METHOD (71) Applicant: DISCO CORPORATION, Tokyo (JP)

(72) Inventors: Senichi Ryo, Tokyo (JP); Yusaku Ito, Tokyo (JP); Tomoaki Endo, Tokyo (JP); Yukinobu Ohura, Tokyo (JP); Kentaro Odanaka, Tokyo (JP)

(73) Assignee: DISCO CORPORATION, Tokyo (JP)

( * ) Notice: Subject to any disclaimer, the term of this patent is extended or adjusted under 35 U.S.C. 154(b) by 0 days. days.

(21) Appl. No.: 15/066,688

(22) Filed: Mar. 10, 2016

(65) Prior Publication Data
US 2016/0266037 A1 Sep. 15, 2016

(30) Foreign Application Priority Data

Mar. 11, 2015 (JP) .................. 2015-048446

(51) Int. Cl.
*G01J 5/00* (2006.01)
*G01N 21/55* (2014.01)
*G01N 21/84* (2006.01)
*H01L 21/66* (2006.01)
*G01N 21/3563* (2014.01)

(52) U.S. Cl.
CPC ......... *G01N 21/55* (2013.01); *G01N 21/8422* (2013.01); *G01N 21/3563* (2013.01); *G01N 2021/8427* (2013.01); *G01N 2021/8433* (2013.01); *H01L 22/12* (2013.01)

(58) Field of Classification Search
CPC ........ G01J 5/20; G01J 5/08; G01J 5/02; G01J 5/10; H04N 5/33
See application file for complete search history.

(56) References Cited

U.S. PATENT DOCUMENTS

2005/0116187 A1* 6/2005 Uda ..................... G01N 21/956
250/559.45
2012/0086797 A1* 4/2012 Furuta ................... B23K 26/38
348/87

FOREIGN PATENT DOCUMENTS

JP 10-305420 11/1998
JP 2007-201178 8/2007

* cited by examiner

*Primary Examiner* — David Porta
*Assistant Examiner* — Mamadou Faye
(74) *Attorney, Agent, or Firm* — Greer Burns & Crain, Ltd.

(57) ABSTRACT

A method detects whether or not a workpiece is coated with a water-soluble protective film. The method includes a preparatory step before detection and a detecting step. The preparatory step includes irradiating with infrared light a first region coated with the water-soluble protective film and a second region not coated with the water-soluble protective film for a reference, receiving the reflected light, and thereby acquiring an intensity of reflection from the first region and an intensity of reflection from the second region; and a threshold determining step of determining a threshold from the intensity of reflection from the first region and the intensity of reflection from the second region at a wavenumber of 3000 cm$^{-1}$ to 3600 cm$^{-1}$. The detecting step includes irradiating a surface of the workpiece with the infrared light, receiving the reflected light, and comparing the thus obtained intensity of reflection with the threshold.

7 Claims, 11 Drawing Sheets

PROTECTIVE FILM DETECTING METHOD

BACKGROUND OF THE INVENTION

Field of the Invention

The present invention relates to a protective film detecting method for detecting a water-soluble protective film with which a work surface of a workpiece such as a semiconductor wafer is coated.

Description of the Related Art

As a method for dividing a wafer such as a semiconductor wafer and an optical device wafer along streets, there has been proposed a method in which a laser beam is applied along streets formed on a workpiece such as a wafer to form laser-processed grooves, and the workpiece is broken along the laser-processed grooves by a mechanical breaking apparatus (see, for example, Japanese Patent Laid-open No. Hei10-305420).

When the workpiece is irradiated with the laser beam along the streets in this processing method, thermal energy is concentrated on irradiated regions to generate debris, which may be deposited on the surfaces of devices, leading to a new problem that the quality of the devices is lowered. In order to solve the problem arising from the deposition of debris, a laser processing machine has been proposed in which a work surface of a workpiece is coated with a water-soluble protective film formed of polyvinyl alcohol or the like, and a laser beam is applied to the workpiece (wafer) through the water-soluble protective film (see, for example, Japanese Patent Laid-open No. 2007-201178).

The water-soluble protective film may need to coat those parts of the work surface of the workpiece at which lowering in device quality may be brought about by deposition of debris. In the laser processing machine disclosed in Japanese Patent Laid-open No. 2007-201178, however, a region or regions not coated with the water-soluble protective film may be generated in the work surface of the workpiece, due to such causes as adhesion of a water-soluble liquid resin (for forming the water-soluble protective film) in a nozzle for jetting the liquid resin, mixing of air bubbles into the liquid resin, etc. Since the problem due to debris is generated in the regions having failed to be coated, it is necessary, after the coating step with the water-soluble protective film, to check whether the desired regions have actually been coated with the water-soluble protective film.

SUMMARY OF THE INVENTION

As a method for checking the conditions of coating with a water-soluble protective film, there is a method in which after a workpiece is coated with the water-soluble protective film, the work surface is irradiated with ultraviolet light or visible light, and the reflected light is received, thereby detecting the region or regions not coated with the water-soluble protective film. In the cases of checking the conditions of coating of a workpiece having a flat surface such as mirror silicon or glass with a water-soluble protective film by such a method, a difference in reflection intensity is observed depending on the presence/absence of the water-soluble protective film, and, therefore, it is easy to detect the conditions of coating with the water-soluble protective film. However, in the case of a workpiece with bumps or patterns on the surfaces thereof yet to be divided into devices, the reflection intensity may be lowered due to scattering by the bumps or patterns or due to a film (composed of polyimide or the like) present on the surfaces. For this reason, there have been cases where it is impossible or very difficult to accurately discriminate a region coated with the water-soluble protective film and a region not coated with the water-soluble protective film from each other.

In addition, there is also a method in which a work surface of a workpiece is irradiated with infrared light, and the reflected light is received, so as to detect the conditions of coating with a water-soluble protective film on the basis of the reflection intensity. In such a case, a region not coated with the water-soluble protective film is used as a reference, and the region coated with the water-soluble protective film and the region not coated with the water-soluble protective film are distinguished from each other on the basis of the difference in reflection intensity between the regions. Where the region not coated with the water-soluble protective film of the workpiece yet to be divided into devices is used as a reference in such a method, however, the reflection intensity varies so greatly depending on the part being used as the reference that it would be impossible or extremely difficult to accurately discern the region coated with the water-soluble protective film and the region not coated with the water-soluble protective film from each other on the basis of only the difference in reflection intensity.

Accordingly, it is an object of the present invention to provide a protective film detecting method by which the influences of the above-mentioned problems can be avoided or mitigated, and the conditions of coating with a water-soluble protective film by a protective film coating apparatus can be precisely examined.

In accordance with an aspect of the present invention, there is provided a protective film detecting method for detecting whether or not a workpiece formed with a bump or a pattern on a surface thereof is coated with a water-soluble protective film, the method including: a reflection intensity acquiring step of irradiating with infrared light having a predetermined wavelength range a reference that has a first region preliminarily coated with the water-soluble protective film and a second region not coated with the water-soluble protective film, receiving reflected light, and acquiring an averaged intensity of reflection from the first region and an averaged intensity of reflection from the second region; a threshold determining step of determining a threshold to be used as a reference for determining whether or not a surface of concern is coated with the water-soluble protective film, from the intensity of reflection from the first region and the intensity of reflection from the second region at a wavenumber of 3000 $cm^{-1}$ to 3600 $cm^{-1}$; and a detection step of sequentially irradiating a surface of the workpiece coated with the water-soluble protective film with the infrared light at a predetermined angle θ, receiving reflected light to acquire an intensity of reflection, comparing the thus acquired reflection intensity with the threshold, and thereby detecting whether or not the surface of concern is coated with the water-soluble protective film.

Preferably, the predetermined angle θ is an angle formed between incident light and the reflected light, and is selected from the range of 0°<θ≤60°.

The above and other objects, features and advantages of the present invention and the manner of realizing them will become more apparent, and the invention itself will best be understood from a study of the following description and appended claims with reference to the attached drawings showing some preferred embodiments of the invention.

DETAILED DESCRIPTION OF THE PREFERRED EMBODIMENTS

Some embodiments of the present invention will be described in detail below, referring to the drawings. The present invention, however, is not limited by the contents of the following description. The components described below include those which can be easily supposed by one skilled in the art, and include those which are substantially the same. Further, the components described below can be combined appropriately. Besides, various omissions, substitution and modifications of the components can be made within the scope of the gist of the present invention.

First Embodiment

Figure 1:
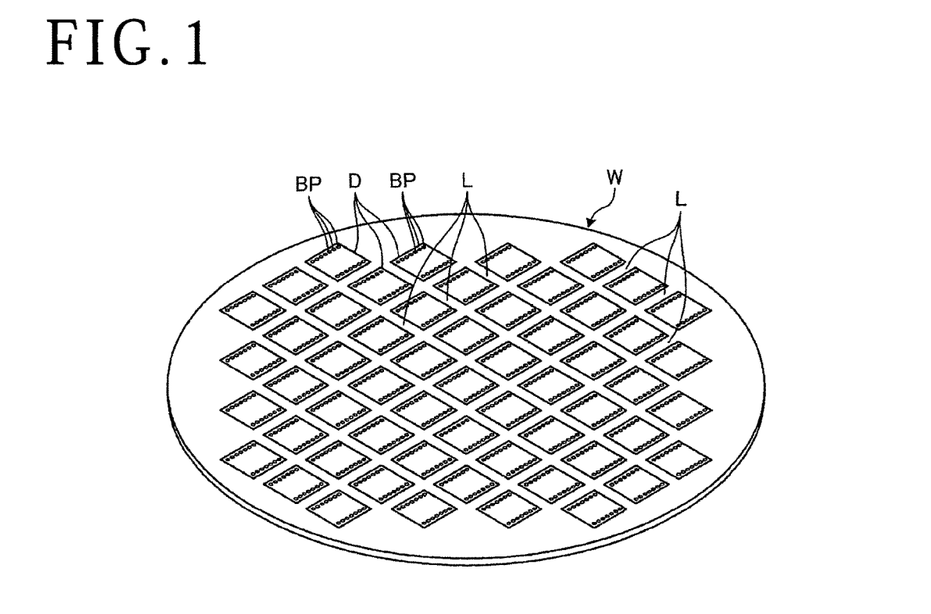
FIG. 1 is a perspective view showing an example of a workpiece on which a water-soluble protective film is to be detected by a protective film detecting method according to a first embodiment of the present invention.
Figure 2:
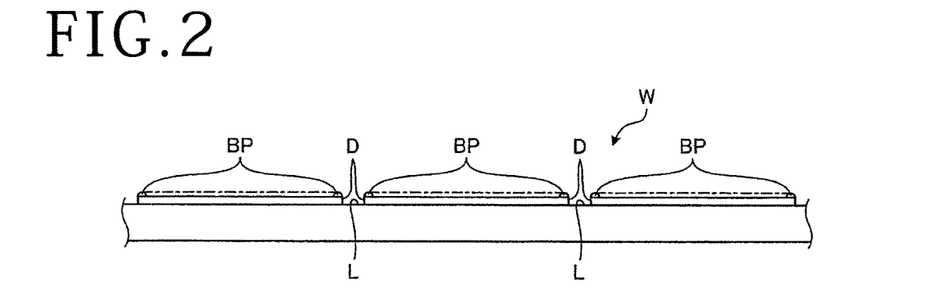
FIG. 2 is a side view of an essential part of the workpiece shown in FIG. 1.
Figure 4:
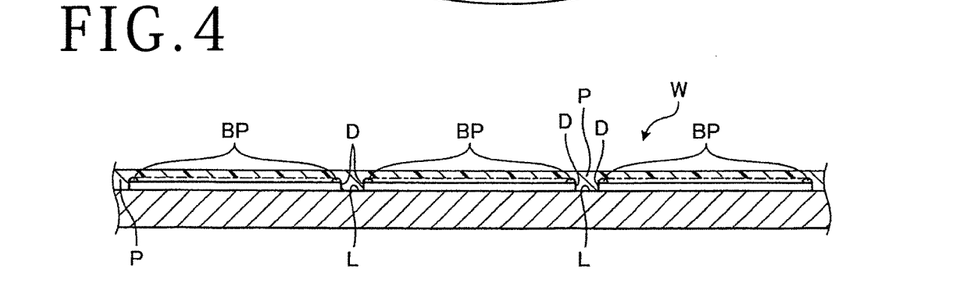
FIG. 4 is a sectional view of an essential part of the workpiece coated with the water-soluble protective film by the protecting film coating apparatus shown in FIG. 3.

A protective film detecting method according to a first embodiment is a method of detecting whether or not a workpiece W, of which an example is shown in FIGS. 1 and 2, is coated with a water-soluble protective film P (shown in FIG. 4). In the first embodiment, the workpiece W is a disk-shaped semiconductor wafer or optical device wafer in which silicon, sapphire, gallium or the like is used as a base material. In the workpiece W, as shown in FIGS. 1 and 2, a plurality of devices D formed on the surface of the workpiece W are partitioned in a grid pattern by a plurality of streets L. Each of the devices D of the workpiece W is formed with a plurality of bumps BP (also called electrodes) projecting from the surface thereof. In other words, the workpiece W is formed with the plurality of bumps BP on the surface thereof. After the surface of the workpiece W is coated with the water-soluble protective film P, the workpiece W is subjected to ablation by applying a laser beam to the streets L by use of a laser processing apparatus. After the workpiece W is subjected to the ablation, the water-soluble protective film P is removed, and the workpiece W is divided along laser-processed grooves formed by the ablation, into the individual devices D.

Here, the water-soluble protective film P is composed of a water-soluble resin including PVA (polyvinyl alcohol), PVP (polyvinyl pyrrolidone) or the like as a base material. The water-soluble protective film P is for restraining debris generated upon the ablation from being deposited on the surfaces of the devices D to lower the quality of the devices D. The water-soluble protective film P is formed to coat the surface of the workpiece W before the laser processing, and is removed from the surface of the workpiece W after the laser processing.

Figure 3:
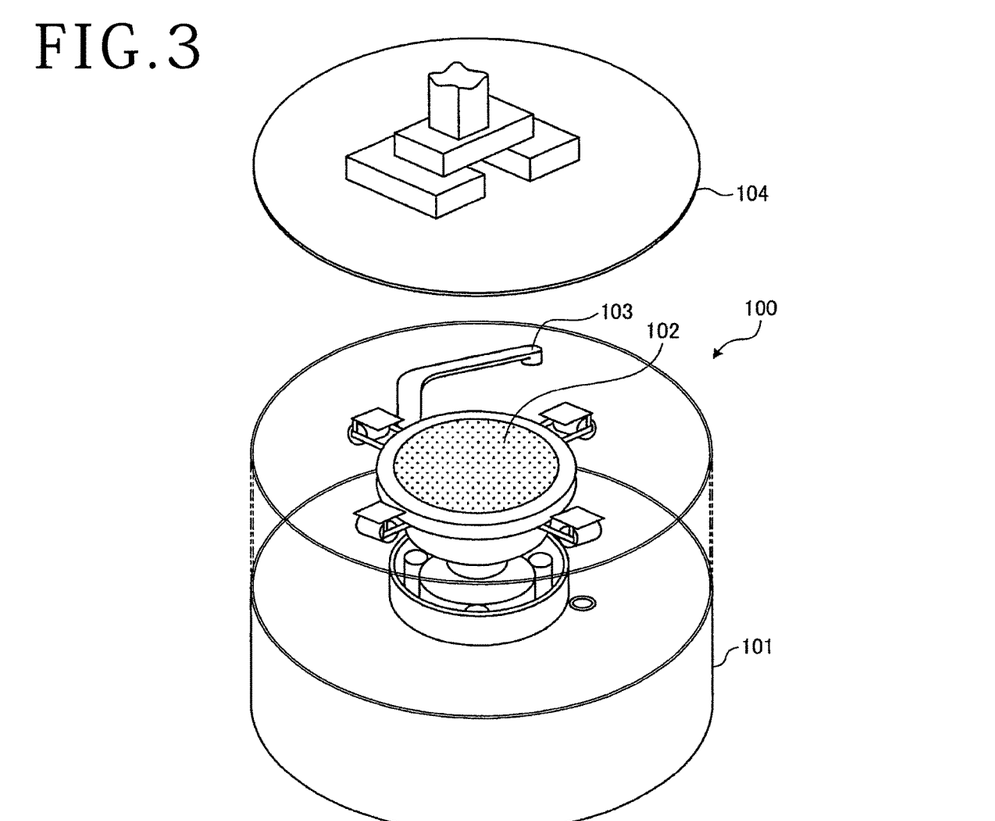
FIG. 3 is a perspective view showing an example of a protective film coating apparatus for coating a surface of the workpiece shown in FIG. 1 with a water-soluble protective film.

For coating the surface of the workpiece W with the water-soluble protective film P and for removing the water-soluble protective film P, there is used, for example, a protective film coating apparatus 100 shown in FIG. 3. As illustrated in FIG. 3, the protective film coating apparatus 100 includes: a housing 101; a rotatable spinner table 102 for holding the workpiece W by suction; an application nozzle 103 for applying a liquid resin for forming the water-soluble protective film P to the surface of the workpiece W suction-held by the spinner table 102; and a washing nozzle (not shown) for removing the water-soluble protective film P from the surface.

The protective film coating apparatus 100 is used as follows. Before coating the surface of the workpiece W with the water-soluble protective film P, the workpiece W yet to be coated with the water-soluble protective film P is placed onto the spinner table 102 through an opening on an upper side of the housing 101, the workpiece W is suction-held onto the spinner table 102, and the spinner table 102 is lowered. Thereafter, the opening on the upper side of the housing 101 of the protective film coating apparatus 100 is closed with a lid 104, the spinner table 102 is rotated about an axis, and, while swinging the application nozzle 103, the liquid resin is dropped from the application nozzle 103 onto the surface of the workpiece W held on the spinner table 102 in such a manner that the liquid resin is applied to the whole part of the surface of the workpiece W by centrifugal forces, whereby the surface is coated with the water-soluble protective film P. After the lapse of a predetermined time, the application nozzle 103 of the protective film coating apparatus 100 is retracted from the position over the spinner table 102, the rotation of the spinner table 102 is stopped, then the spinner table 102 is raised, and the opening on the upper side of the housing 101 is opened by removing the lid 104. Then, the suction holding of the workpiece W onto the spinner table 102 of the protective film coating apparatus 100 is released, and the workpiece W coated with the water-soluble protective film P as depicted in FIG. 4 is taken out from the position on the spinner table 102 by way of the opening on the upper side of the housing 101. It is demanded that the whole part of the surface of the workpiece W be coated with the water-soluble protective film P by the protective film coating apparatus 100.

In addition, at the time of removing the water-soluble protective film P from the surface of the workpiece W by using the protective film coating apparatus 100, the workpiece W to be deprived of the water-soluble protective film P is placed onto the spinner table 102 by way of the opening on the upper side of the housing 101, the workpiece W is suction-held onto the spinner table 102, and the spinner table 102 is lowered. Thereafter, the opening on the upper side of the housing 101 of the protective film coating apparatus 100 is closed with the lid 104, the spinner table 102 is rotated about the axis, and a washing liquid is dropped from the washing nozzle onto the surface of the workpiece W held on the spinner table 102 in such a manner that the surface of the workpiece W is washed with the washing liquid under centrifugal forces, whereby the water-soluble protective film P is removed. After the lapse of a predetermined time, the washing nozzle of the protective film coating apparatus 100 is retracted from the position over the spinner table 102, the rotation of the spinner table 102 is stopped, the spinner table 102 is raised, and the opening on the upper side of the housing 101 is opened by removing the lid 104. Then, the suction holding of the workpiece W by the spinner table 102 of the protective film coating apparatus 100 is released, and the workpiece W deprived of the water-soluble protective film P is taken out from the position on the spinner table 102 by way of the opening on the upper side of the housing 101.

Figure 5:
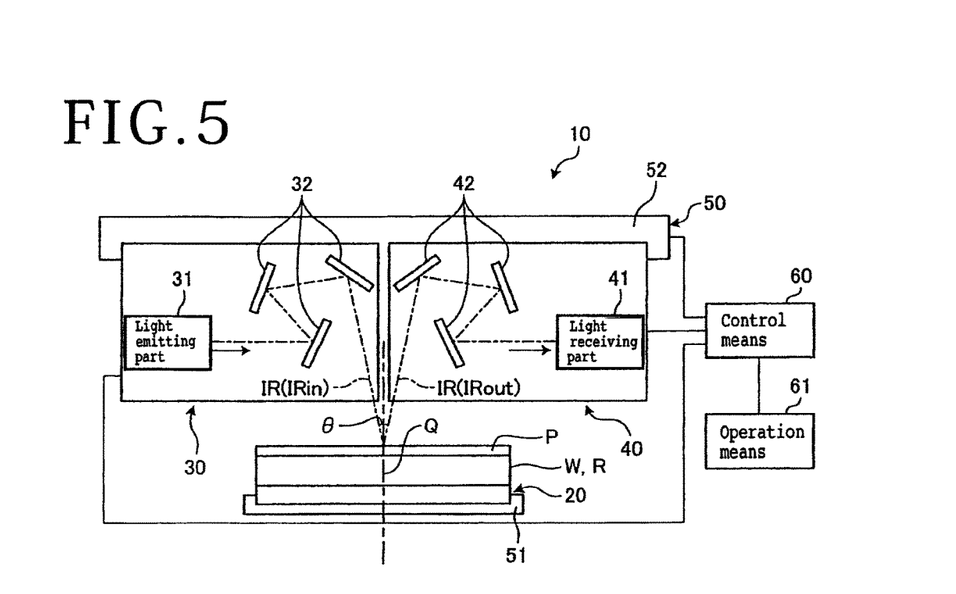
FIG. 5 is a diagram showing an example of a configuration of a detection device for use in the protective film detecting method according to the first embodiment.

The protective film detecting method according to the first embodiment is a method for detecting the presence or absence of a water-soluble protective film P on a surface of a workpiece W by using a detection device 10 shown in FIG. 5. Specifically, the detection device 10 is a device for detecting whether or not the whole part of the surface of the workpiece W is coated with the water-soluble protective film P. The detection device 10 shown in FIG. 5 is a device that irradiates each of the workpiece W, which is to be divided into devices D and is an object of detection, and a reference R (shown in FIG. 7) with infrared light IR, and detects the presence/absence of the water-soluble protective film P on the workpiece W on the basis of the intensities of reflection from the workpiece W and the reference R.

Figure 7:
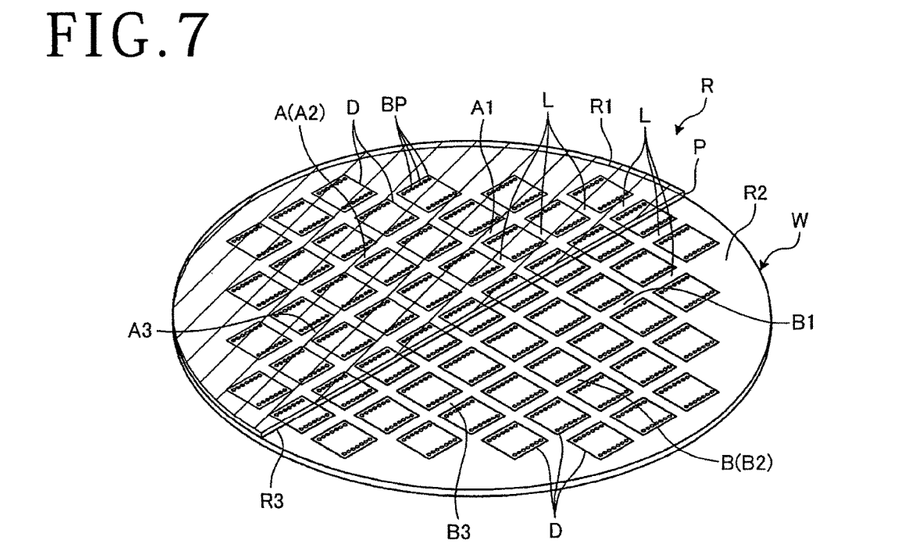
FIG. 7 is a perspective view showing a reference for use in a preparatory step in the protective film detecting method according to the first embodiment.

As the reference R, in the first embodiment, there is used one wherein a first region R1 of a surface of a workpiece W is preliminarily coated with a water-soluble protective film P whereas a second region R2 of the surface exclusive of the first region R1 is not coated with the water-soluble protective film P (namely, the surface is exposed in the second region R2), as shown in FIG. 7. In other words, the reference R has the first region R1 preliminarily coated with the water-soluble protective film P and the second region R2 not coated with the water-soluble protective film P. In the first embodiment, the first region R1 and the second region R2 of the reference R are arranged at such positions as to bisect the surface of the workpiece W, and are partitioned from each other, with a boundary coinciding with a straight line R3 passing the center of the surface of the workpiece W.

As shown in FIG. 5, the detection device 10 includes: a holding table 20 for holding each of the workpiece W and the reference R; an infrared light irradiation section 30; an infrared light receiving section 40; driving means 50; and control means 60. The infrared light irradiation section 30 irradiates the workpiece W and the reference R with infrared light IR having a predetermined wavelength range, and includes a light emitting part 31 for emitting the infrared light IR, and a plurality of optical parts 32 for irradiating each of the workpiece W and the reference R held on the holding table 20 with the infrared light IR. In the first embodiment, the light emitting part 31 emits infrared light IR that at least includes a wavelength range in terms of wavenumber of 3000 $cm^{-1}$ to 3600 $cm^{-1}$. Note that the wavenumber herein means the reciprocal of wavelength.

In addition, the infrared light irradiation section 30 is configured such that the wavelength of the infrared light IR with which to irradiate the workpiece W and the reference R held on the holding table 20 can be varied. Further, in the first embodiment, the infrared light irradiation section 30 applies the infrared light IR to a position spaced from the center of the surface of each of the workpiece W and the reference R held on the holding table 20.

The infrared light receiving section 40 receives the infrared light IR emitted by the infrared light irradiation section 30 and reflected on the surface of each of the workpiece W and the reference R, and outputs information indicative of reflection intensity to the control means 60. The infrared light receiving section 40 includes a light receiving part 41 for receiving the infrared light IR, and a plurality of optical parts 42 for guiding to the light receiving part 41 the infrared light IR that is reflected on the surface of each of the workpiece W and the reference R held on the holding table 20. In the first embodiment, the light receiving part 41 receives infrared light IR that includes a wavelength range in terms of wavenumber of 3000 $cm^{-1}$ to 3600 $cm^{-1}$.

The driving means 50 includes: a rotational driving part 51 that rotates the holding table 20 about an axis Q; and a rectilinear driving part 52 by which the distance between the infrared light irradiation section 30 and the infrared light receiving section 40 can be varied. The rotational driving part 51 includes a motor (not shown) or the like, and rotates the holding table 20 about the axis Q so as to vary the position at which each of the workpiece W and the reference R is irradiated with the infrared light IR. The rectilinear driving part 52 moves the infrared light irradiation section 30 and the infrared light receiving section 40 along a horizontal direction such that the horizontal distance between the infrared light irradiation section 30 and the infrared light receiving section 40 can be varied, so as thereby to change the angle θ between an incident light IRin of the infrared light IR radiated to each of the workpiece W and the reference R by the infrared light irradiation section 30 and a reflected light IRout of the infrared light IR reflected on the surface of each of the workpiece W and the reference R. Note that in the first embodiment, the optical parts 32 of the infrared light irradiation section 30 and the optical parts 42 of the infrared light receiving section 40 are configured to be adjusted in their orientations according to the distance between the infrared light irradiation section 30 and the infrared light receiving section 40 in such a manner that the reflected light IRout of the infrared light IR radiated by the infrared light irradiation section 30 can be received by the infrared light receiving section 40 even when the distance between the infrared light irradiation section 30 and the infrared light receiving section 40 is changed by the rectilinear driving part 52.

The control means 60 controls the above-mentioned components of the detection device 10 so as to cause the detection device 10 to perform the protective film detecting method according to the first embodiment. Note that the control means 60 is composed mainly of a microprocessor (not shown) including a processing means (composed of a CPU or the like), ROM, RAM and the like, and is connected to display means (not shown) for displaying the states of a processing operation, and operation means 61 used by an operator for registration of information on processing and the like.

A detecting operation of the detection device 10 according to the first embodiment, or the protective film detecting method according to the first embodiment, will be described below. The protective film detecting method according to the first embodiment is a method of detecting whether or not a workpiece W formed with bumps BP on a surface thereof is coated with a water-soluble protective film P.

Figure 6:
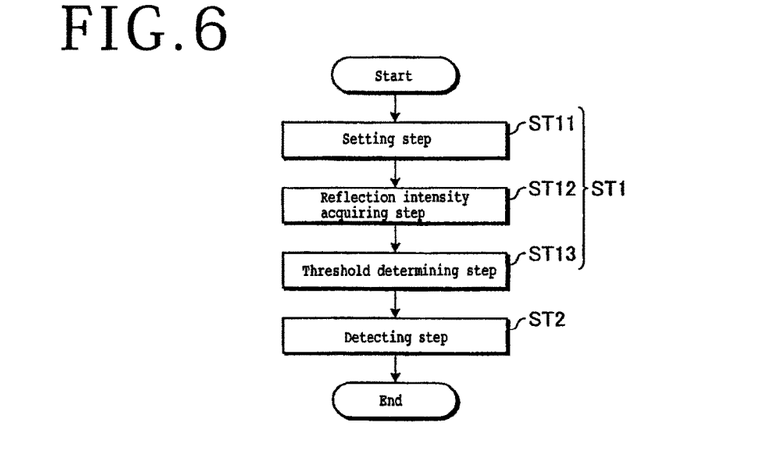
FIG. 6 is a flow chart showing an example of the protective film detecting method according to the first embodiment.

As shown in FIG. 6, the protective film detecting method includes a setting step ST11, a reflection intensity acquiring step ST12, a threshold determining step ST13, and a detecting step ST2 (corresponding to the detection step). In the protective film detecting method, first, information on the contents of detection is registered in the control means 60 by the operator, and the detection device 10 starts a detecting operation when a start command for the detecting operation is given by the operator.

The setting step ST11 is a step of setting a wavelength of infrared light IR used in detecting the presence or absence of the water-soluble protective film P on the workpiece W and an angle θ formed between the incident light IRin and the reflected light IRout of the infrared light IR as a predetermined angle. In the setting step ST11, the operator causes the reference R to be held on the holding table 20 of the detection device 10. Note that in this instance, the first region R1 and the second region R2 are made to face the infrared light irradiation section 30 and the infrared light receiving section 40.

Then, when the reference R is held on the holding table 20, the control means 60 causes the driving means 50 to change the angle θ and causes the wavelength of the infrared light IR radiated from the infrared light irradiation means 30 to be changed, in such a manner that the infrared light IR is radiated, for example, to a predetermined position A (shown in FIG. 7) in the first region R1 and the reflected light IRout is received. Then, the control means 60 stores the wavelength of the infrared light IR, the angle θ and the reflection intensity of the reflected light IRout in the manner of one-to-one correspondence. Thereafter, the control means 60 causes the driving means 50 to rotate the holding table 20 about the axis Q, causes the driving means 50 to change the angle θ and causes the wavelength of the infrared light IR radiated from the infrared light irradiation section 30 to be changed, in such a manner that the infrared light IR is radiated, for example, to a predetermined position B (shown in FIG. 7) in the second region R2 and the reflected light IRout is received. Then, the control means 60 stores the wavelength of the infrared light IR, the angle θ and the reflection intensity of the reflected light IRout in the manner of one-to-one correspondence. The control means 60 causes the infrared light IR in a wavelength range in terms of wavenumber of 3000 $cm^{-1}$ to 3600 $cm^{-1}$ to be radiated and received, and causes the angle θ to be varied within the range of 0°<θ≤60°. Thus, the predetermined angle θ is the angle θ formed between the incident light IRin and the reflected light IRout, and is selected from the range of 0°<θ≤60°. Thereafter, the control means 60 determines and stores that combination of the wavelength of the infrared light IR and the angle θ which causes the difference between the reflection intensity at the position A in the first region R1 and the reflection intensity at the position B in the second region R2 to become the greatest or become greater than a predetermined value, after which the control means 60 proceeds to the reflection intensity acquiring step ST12. Besides, in the present invention, in the setting step ST11, the reflection intensity may be acquired with respect to a plurality of points in the first region R1, the reflection intensity may be acquired with respect to a plurality of points in the second region R2, and then the angle θ may be determined on the basis of differences in reflection intensity. Further, the difference in reflection intensity may be based on the average of reflection intensities with respect to a plurality of points (or the sum of the reflection intensities with respect to the plurality of points).

The reflection intensity acquiring step ST12 is a step in which a reference R having the first region R1 and a reference R having the second region R2 are irradiated with infrared light IR having a predetermined wavelength range (at least inclusive of a wavelength range in terms of wavenumber of 3000 $cm^{-1}$ to 3600 $cm^{-1}$), the reflected light IRout is received, and an averaged reflection intensity with respect to the first region R1 and an averaged reflection intensity with respect to the second region R2 are acquired. Specifically, in the reflection intensity acquiring step ST12, the control means 60 first acquires the intensities of reflection from a plurality of positions A1, A2 and A3 in the first region R1 of the reference R and the intensities of reflection from a plurality of positions B1, B2 and B3 in the second region R2 of the reference R. In the first embodiment, the control means 60, using the combinations of the wavelength and the angle θ having been stored in the setting step ST11, causes the infrared light IR to be radiated to the three positions A1, A2 and A3 in the first region R1 and the three positions B1, B2 and B3 in the second region R2 in an arbitrary order, acquires and stores the reflection intensities of the reflected light IRout of the infrared light IR from each of the positions A1, A2, A3, B1, B2 and B3, and then proceeds to the threshold determining step ST13. Note that in the reflection intensity acquiring step ST12, the intensities of reflection from the plurality of positions A1, A2 and A3 in the first region R1 of the reference R and the intensities of reflection from the plurality of positions B1, B2 and B3 in the second region R2 of the reference R are acquired, whereby an averaged reflection intensity with respect to the first region R1 and an averaged reflection intensity with respect to the second region R2 are acquired.

The threshold determining step ST13 is a step of determining a threshold C to be used as a reference for determination of whether or not a surface of concern is coated with the water-soluble protective film P, from the reflection intensities with respect to the first region R1 and the second region R2 at a wavenumber of 3000 cm$^{-1}$ to 3600 cm$^{-1}$. Specifically, the control means 60 calculates an average Aave of the reflection intensities of the reflected light IRout from the positions A1, A2 and A3 in the first region R1 and an average Bave of the reflection intensities of the reflected light IRout from the positions B1, B2 and B3 in the second region R2, the reflection intensities being acquired in the reflection intensity acquiring step ST12. The control means 60, for example, calculates and stores a value between the average Aave and the average Bave as the threshold C. Then, the operator removes the reference R from the holding table 20, and the control means 60 proceeds to the detecting step ST2.

Note that in the present invention, the threshold C may be appropriately selected from values between the average Aave and the average Bave. Alternatively, the threshold C may be appropriately selected on the basis of, for example, the minimum one of the reflection intensities of the reflected light IRout from the positions A1, A2 and A3 and, for example, the maximum one of the reflection intensities of the reflected light IRout from the positions B1, B2 and B3. Further, in the present invention, the threshold C may be appropriately selected on the basis of the sum of the reflection intensities of the reflected light IRout from the positions A1, A2 and A3 and the sum of the reflection intensities of the reflected light IRout from the positions B1, B2 and B3. Note that the setting step ST11, the reflection intensity acquiring step ST12 and the threshold determining step ST13 constitute a preparatory step ST1 before detection. Namely, the preparatory step ST1 includes the setting step ST11, the reflection intensity acquiring step ST12 and the threshold determining step ST13. In addition, in the present invention, in the case where the angle θ is determined on the basis of the reflection intensities with respect to the plurality of points in the first region R1 and the plurality of points in the second region R2 in the setting step ST11, the reflection intensities with respect to a predetermined wavelength range may not be again acquired in the reflection intensity acquiring step ST12, and the threshold determining step ST13 may be conducted using the reflection intensities acquired in the setting step ST11.

The detecting step ST2 is a step in which the surface of the workpiece W coated with the water-soluble protective film P is sequentially irradiated with the infrared light IR at the angle θ as the predetermined angle, the reflected light IRout is received, and the reflection intensity is compared with the threshold C, whereby it is detected whether or not the surface of concern is coated with the water-soluble protective film P. In the detecting step ST2, the operator causes the workpiece W to be held on the holding table 20 of the detection device 10. Note that in this instance, the water-soluble protective film P with which the surface of the workpiece W is coated is made to face the infrared light irradiation section 30 and the infrared light receiving section 40.

Then, when the workpiece W is held on the holding table 20, the control means 60 sequentially radiates the infrared light IR to a plurality of predetermined positions of the workpiece W, to acquire reflection intensities. In the first embodiment, the control means 60 radiates the infrared light IR to those positions of the workpiece W which correspond to the positions A1, A2 and A3 and positions B1, B2 and B3 of the reference R in combinations of the wavelength and the angle θ that have been stored in the setting step ST11, in an arbitrary order, and the control means 60 acquires and stores the reflection intensities of the reflected light IRout of the infrared light IR from those positions.

The control means 60, if the intensity of reflection from a position is not less than the threshold C, detects that the position is not coated with the water-soluble protective film P. If the intensity of reflection from a position is less than the threshold C, on the other hand, the control means 60 detects that the position is coated with the water-soluble protective film P. The control means 60, if the intensities of reflection from all positions are less than the threshold C, detects that the whole part of the surface of the workpiece W is coated with the water-soluble protective film P. If the intensity of reflection from at least one of the positions is not less than the threshold C, on the other hand, the control means 60 detects that the whole part of the surface of the workpiece W is not coated with the water-soluble protective film P, and finishes the protective film detecting method. Note that in the detecting step ST2, the detection of the water-soluble protective film P may be conducted for a plurality of workpieces W. Note that in the case where the threshold C is selected in the threshold determining step ST13 on the basis of the sum of the reflection intensities of the reflected light IRout from the plurality of positions A1, A2 and A3 in the first region R1 and the sum of the reflection intensities of the reflected light IRout from the plurality of positions B1, B2 and B3 in the second region R2, detection in the detecting step ST2 may be conducted in such a manner that the sum of the intensities of reflection of the reflected light IRout from those positions of the workpiece W which correspond to the positions A1, A2 and A3 or those positions of the workpiece W which correspond to the positions B1, B2 and B3 is determined, and if the sum is not less than the threshold C, it is detected that the whole part of the surface of the workpiece W is not coated with the water-soluble protective film P, whereas if the sum is less than the threshold C, it is detected that the whole part of the surface of the workpiece W is coated with the water-soluble protective film P. In addition, it may be detected that the surface of concern is not coated with the water-soluble protective film P, by comparing the threshold C with the respective intensities of reflection from a plurality of positions, like in other examples.

Note that when a region to be coated with the water-soluble protective film P is found not to be coated with the water-soluble protective film P as mentioned above, the water-soluble protective film P is once removed by the protective film coating apparatus 100, and the surface of the workpiece W is again coated with the water-soluble protective film P. Thereafter, whether or not the surface of concern is coated with the water-soluble protective film P is detected by the aforementioned protective film detecting method.

In the protective film detecting method according to the first embodiment, in the preparatory step ST1, the threshold C is determined from the intensities of reflection from the plurality of positions A1, A2 and A3 in the first region R1 of the reference R and the plurality of positions B1, B2 and B3 in the second region R2 of the reference R. Therefore, the threshold C can be determined on the basis of the reflection intensity that varies depending on the presence or absence of the water-soluble protective film P and on the detection position. In the protective film detecting method, since the threshold C is determined from the intensities of reflection from the plurality of positions A1, A2, A3, B1, B2 and B3, even if there are variabilities of the reflection intensity among the detection positions in the reference R, the variabilities of the reflection intensity are averaged, so that a value suitable for determination of the presence/absence of the water-soluble protective film P on the workpiece W yet to be divided into the devices D can be used as the threshold C. Therefore, it is possible by the protective film detecting method to accurately detect whether or not a surface of concern is coated with the water-soluble protective film P. Consequently, it is possible by the protective film detecting method to precisely confirm the conditions of coating with the water-soluble protective film P by the protective film coating apparatus 100.

In addition, since the threshold C is determined on the basis of the reflection intensity of the infrared light IR having a wavelength range in terms of wavenumber of 3000 $cm^{-1}$ to 3600 $cm^{-1}$, infrared light IR that is easily absorbed by the OH group or NH group present as substituent group in the water-soluble polymer or by bonds of the group with water is used for the detection of the presence/absence of the water-soluble protective film P. Accordingly, it is possible by the protective film detecting method to accurately detect the presence/absence of the water-soluble protective film P.

Further, in the protective film detecting method, since the angle θ is selected from within the range of 0°<θ≤60°, the difference in reflection intensity depending on the presence/absence of the water-soluble protective film P can be secured in a reliable manner, so that the presence/absence of the water-soluble protective film P can be accurately detected. In addition, in the protective film detecting method, the angle θ between the incident light IRin and the reflected light IRout and the wavelength of the infrared light IR which are to be used in the detection step are set in the setting step ST11 on the basis of the intensity of reflection from the position A in the first region R1 of the reference R and the intensity of reflection from the position B in the second region R2 of the reference R. This ensures that the detection step can be carried out under conditions suitable for detection of the water-soluble protective film P. Consequently, by setting an angle θ and a wavelength of the infrared light IR that correspond to a condition where the difference between the intensity of reflection from the position A in the first region R1 of the reference R and the intensity of reflection from the position B in the second region R2 of the reference R becomes the greatest, it is possible to detect the water-soluble protective film P under optimum conditions.

Furthermore, the protective film detecting method uses a reference R wherein the first region R1 of the surface of a workpiece W is coated with the water-soluble protective film P whereas the second region R2 of the surface is not coated with the water-soluble protective film P. Thus, in the protective film detecting method, a reference R including the workpiece W as an object of detection is used, and, accordingly, the presence/absence of the water-soluble protective film P can be detected accurately.

Second Embodiment

Figure 8:
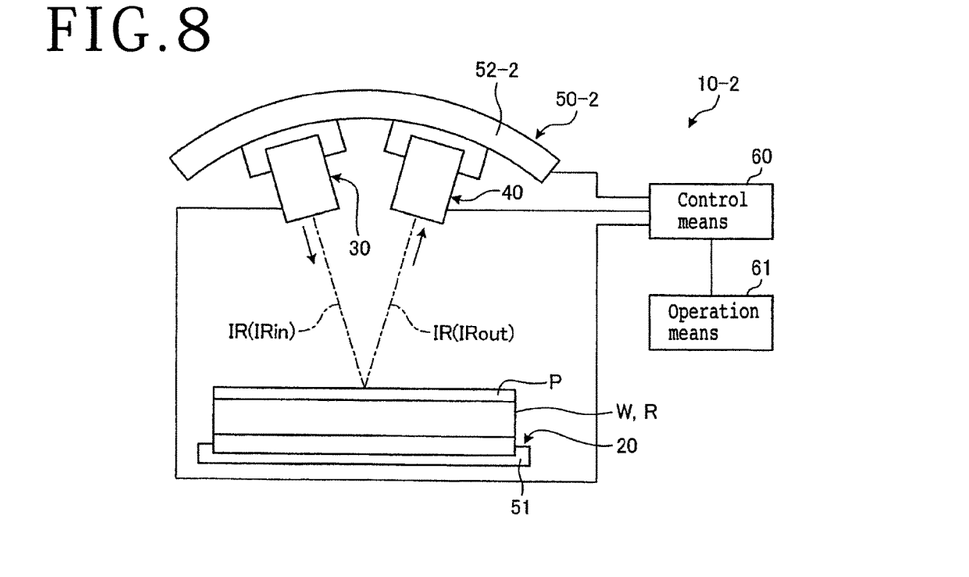
FIG. 8 is a diagram showing an example of a configuration of a detection device for use in a protective film detecting method according to a second embodiment of the present invention.

A protective film detecting method according to a second embodiment of the present invention will be described, on the basis of the drawing. FIG. 8 is a diagram showing an example of a configuration of a detection device for use in the protective film detecting method according to the second embodiment. Note that in FIG. 8, the same parts as those in the first embodiment are denoted by the same reference symbols as used above, and descriptions of the same parts will be omitted.

A detection device 10-2 for use in the protective film detecting method according to the second embodiment includes an infrared light irradiation section 30 and an infrared light receiving section 40 in which optical parts 32 and 42 are so configured that the direction of infrared light IR cannot be varied. Driving means 50-2 of the detection device 10-2 includes a rotational driving part 51, and an arcuate driving part 52-2 that moves the infrared light irradiation section 30 and the infrared light receiving section 40 along a circular arc, with the center at that position on the surface of each of the workpiece W and the reference R held on the holding table 20 which is irradiated with the infrared light IR from the infrared light irradiation section 30.

In the protective film detecting method according to the second embodiment, also, the conditions of coating with the water-soluble protective film P by the protective film coating apparatus 100 can be precisely confirmed, like in the first embodiment.

Third Embodiment

Figure 9:
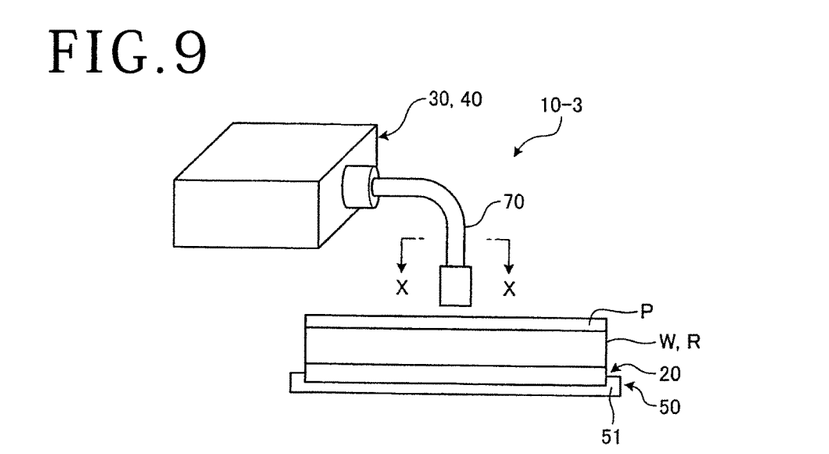
FIG. 9 is a view showing an example of a configuration of a detection device for use in a protective film detecting method according to a third embodiment of the present invention.
Figure 10:
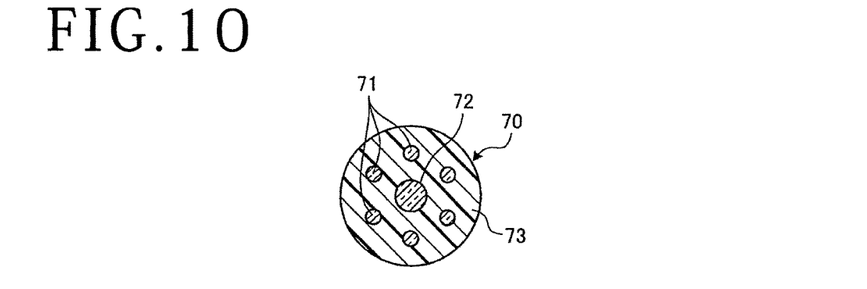
FIG. 10 is a sectional view taken along line X-X of FIG. 9.

A protective film detecting method according to a third embodiment of the present invention will be described below, on the basis of the drawings. FIG. 9 is a diagram showing an example of a configuration of a detection device for use in the protective film detecting method according to the third embodiment. FIG. 10 is a sectional view taken along line X-X of FIG. 9. Note that in FIGS. 9 and 10, the same parts as those in the first embodiment are denoted by the same reference symbols as used above, and descriptions of the same parts will be omitted.

A detection device 10-3 for used in the protective film detecting method according to the third embodiment includes an infrared light irradiation section 30 and an infrared light receiving section 40 wherein infrared light IR is radiated and a reflected light IRout of the infrared light IR is received through a single optical fiber cable 70, as shown in FIG. 9. In the third embodiment, the optical fiber cable 70 includes: a plurality of irradiation optical fibers 71 for guiding infrared light IR emitted by the infrared light irradiation section 30 to each of a workpiece W and a reference R held on the holding table 20; a light receiving optical fiber 72 for receiving a reflected light IRout of the infrared light IR reflected on a surface of each of the workpiece W and the reference R and guiding the reflected light IRout to the infrared light receiving section 40; and a covering section 73 for covering the irradiation optical fibers 71 and the light receiving optical fiber 72. The light receiving optical fiber 72 is disposed in the center of the optical fiber cable 70, and the plurality of irradiation optical fibers 71 are disposed at intervals along the circumferential direction of a circle centered on the light receiving optical fiber 72. This configuration ensures that the detection device 10-3 according to the third embodiment is configured to have a very small value of the angle θ. Besides, in the setting step ST11 in the protective film detecting method according to the third embodiment, the angle θ is not changed, and the wavelength of the infrared light IR for irradiation therewith is varied, to thereby determine a suitable wavelength of the infrared light IR.

In the protective film detecting method according to the third embodiment, also, the conditions of coating with the water-soluble protective film P by the protective film coating apparatus 100 can be precisely confirmed, like in the first embodiment. Besides, in the protective film detecting method according to the third embodiment, since the suitable wavelength of the infrared light IR is determined without determining the angle θ in the setting step ST11, the time required for the setting step ST11 can be shortened.

[Modification]

Figure 11:
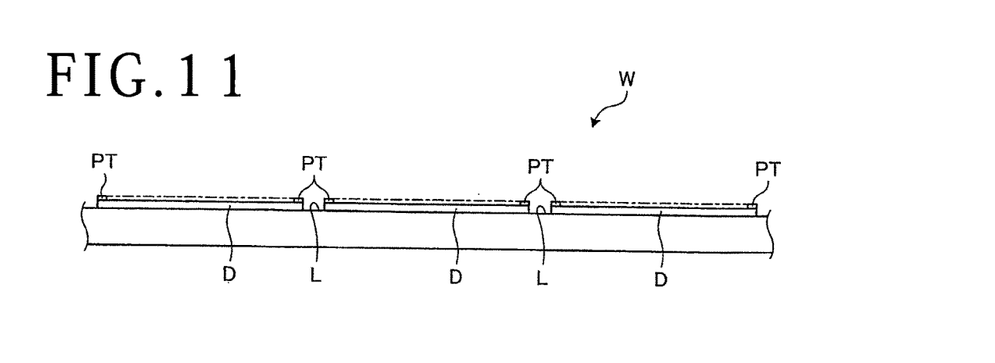
FIG. 11 is a side view of an essential part of a workpiece on which a water-soluble protective film is to be detected by a protective film detecting method according to a modification of the first to third embodiments.

A protective film detecting method according to a modification of the first to third embodiments of the present invention will be described, on the basis of the drawings. FIG. 11 is a side view of an essential part of a workpiece on which a water-soluble protective film is to be detected by the protective film detecting method according to the modification of the first to third embodiments. In FIG. 11, the same parts as those in the first to third embodiments are denoted by the same reference symbols as used above, and descriptions of the same parts will be omitted.

A workpiece W on which a water-soluble protective film P is to be detected by the protective film detecting method according to the modification of the first to third embodiments includes patterns PT of conductive metal on surfaces of devices D. The pattern PT is projecting from the surface of the device D. Thus, the protective film detecting method according to the present invention is a method for detecting whether or not the workpiece W formed with bumps BP and the patterns PT on the surface thereof is coated with the water-soluble protective film P. In the protective film detecting method according to the modification, also, the conditions of coating with the water-soluble protective film P by the protective film coating apparatus 100 can be precisely confirmed, like in the first embodiment.

In addition, while the actual workpiece W having the first region R1 coated with the water-soluble protective film P and the second region R2 not coated with the water-soluble protective film P is used as the reference R in the aforementioned first to third embodiments and modification, the present invention is not limited to this configuration. In the present invention, a disk a surface of which is mirror-like in form and which is formed of gold or the like may be used as the reference R. Besides, a body having only the first region R1 (a body of which entire part of a surface is coated with the water-soluble protective film P) and a body having only the second region R2 (a body of which the whole part of a surface is free of the water-soluble protective film P) may be used as the reference R. Further, in the present invention, the reflection intensity acquired in the setting step ST11 and/or the reflection intensity acquiring step ST12 may be subjected to normalization with the reflection intensity regarding a gold mirror (division of an actual reflection intensity by the reflection intensity regarding the gold mirror).

Figure 12:
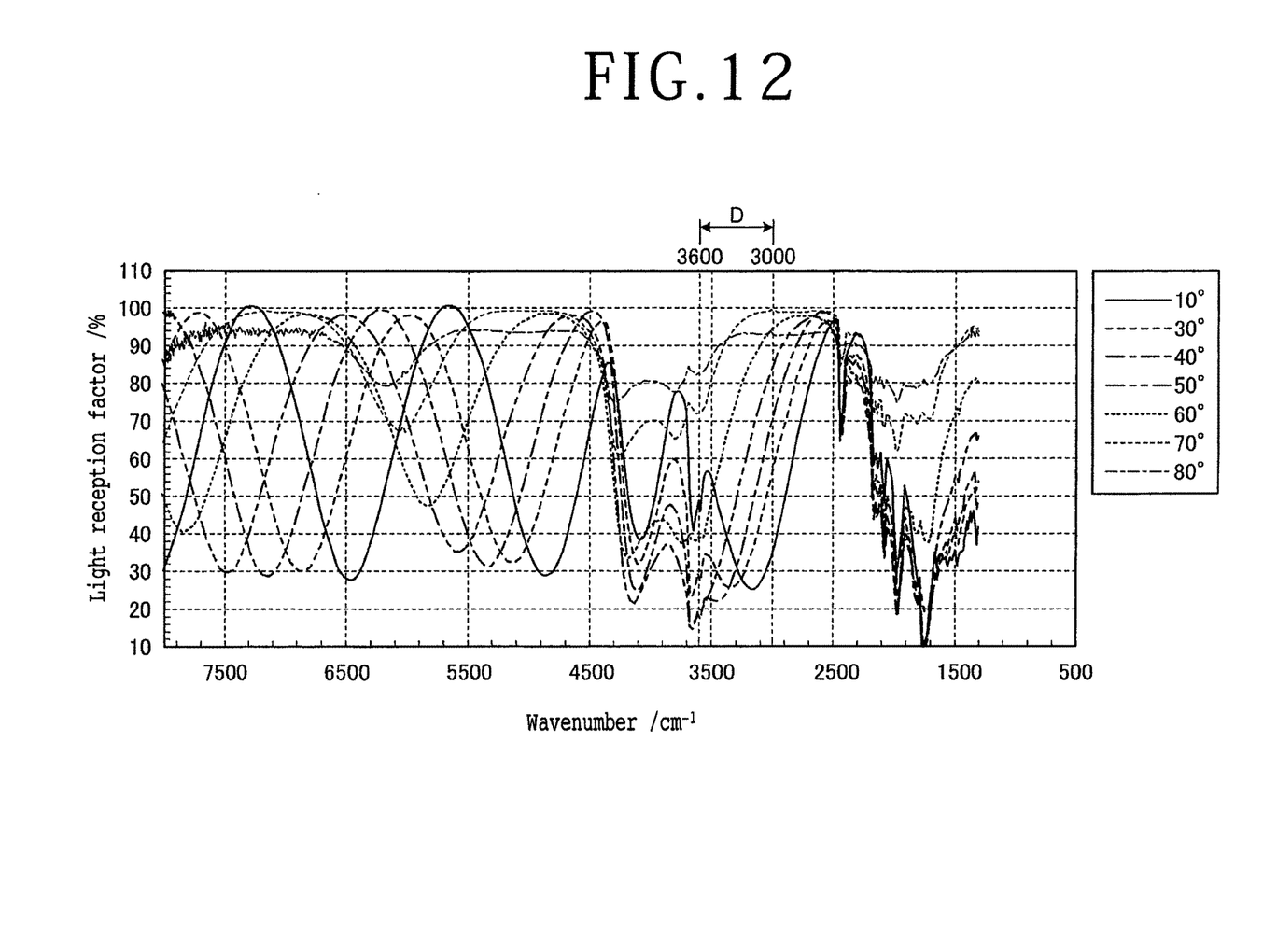
FIG. 12 is a diagram showing intensity of reflection from a water-soluble protective film on a workpiece in relation to intensity of reflection from a first region of a reference, in the case where workpieces not formed with any bump or pattern are used as the reference and the workpiece and where an angle of infrared light at each wavelength is varied.
Figure 13:
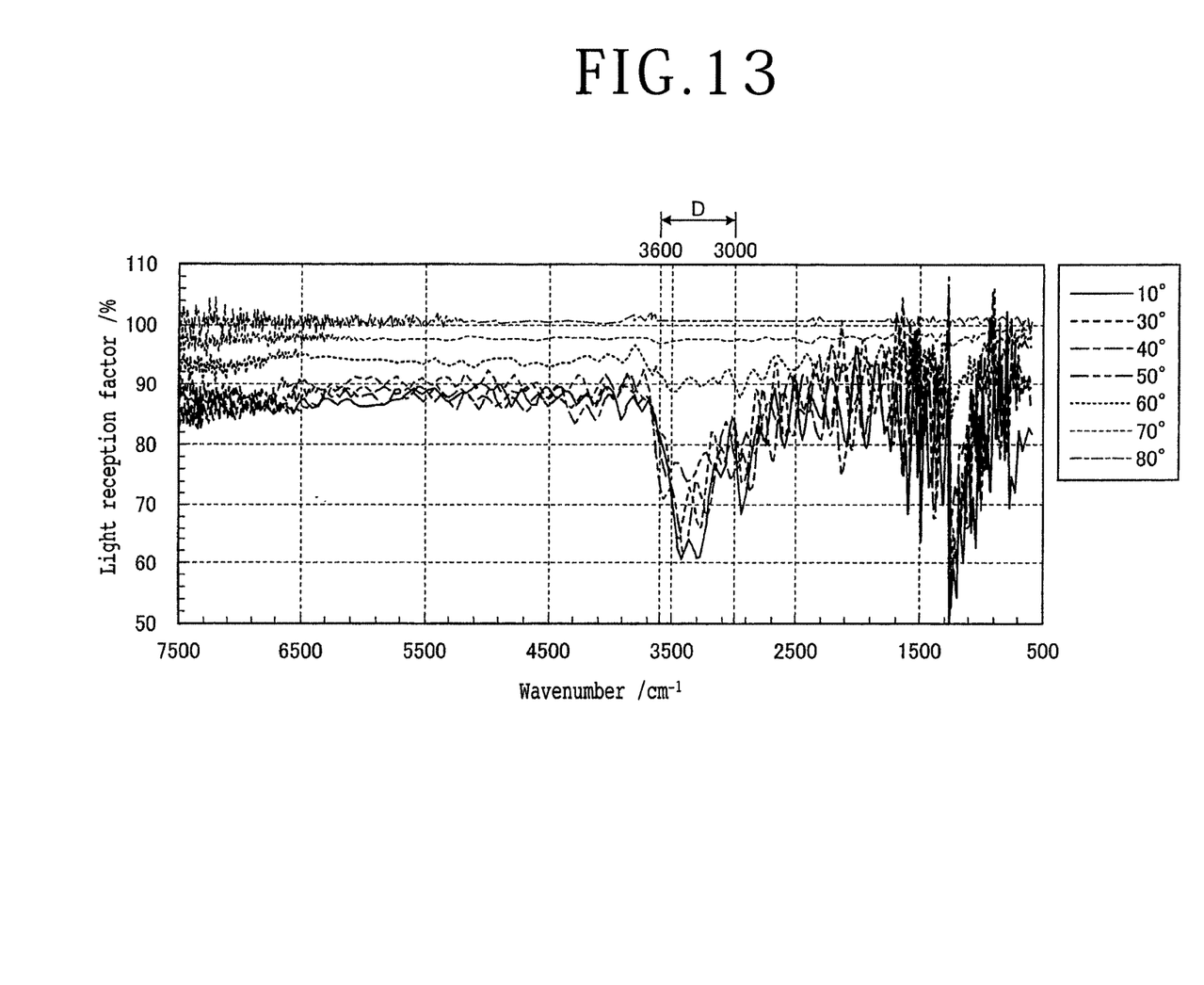
FIG. 13 is a diagram showing intensity of reflection from a water-soluble protective film on a workpiece in relation to intensity of reflection from a first region of a reference, in the case where workpieces formed with bumps are used as the reference and the workpiece and where an angle of infrared light at each wavelength is varied.
Figure 14:
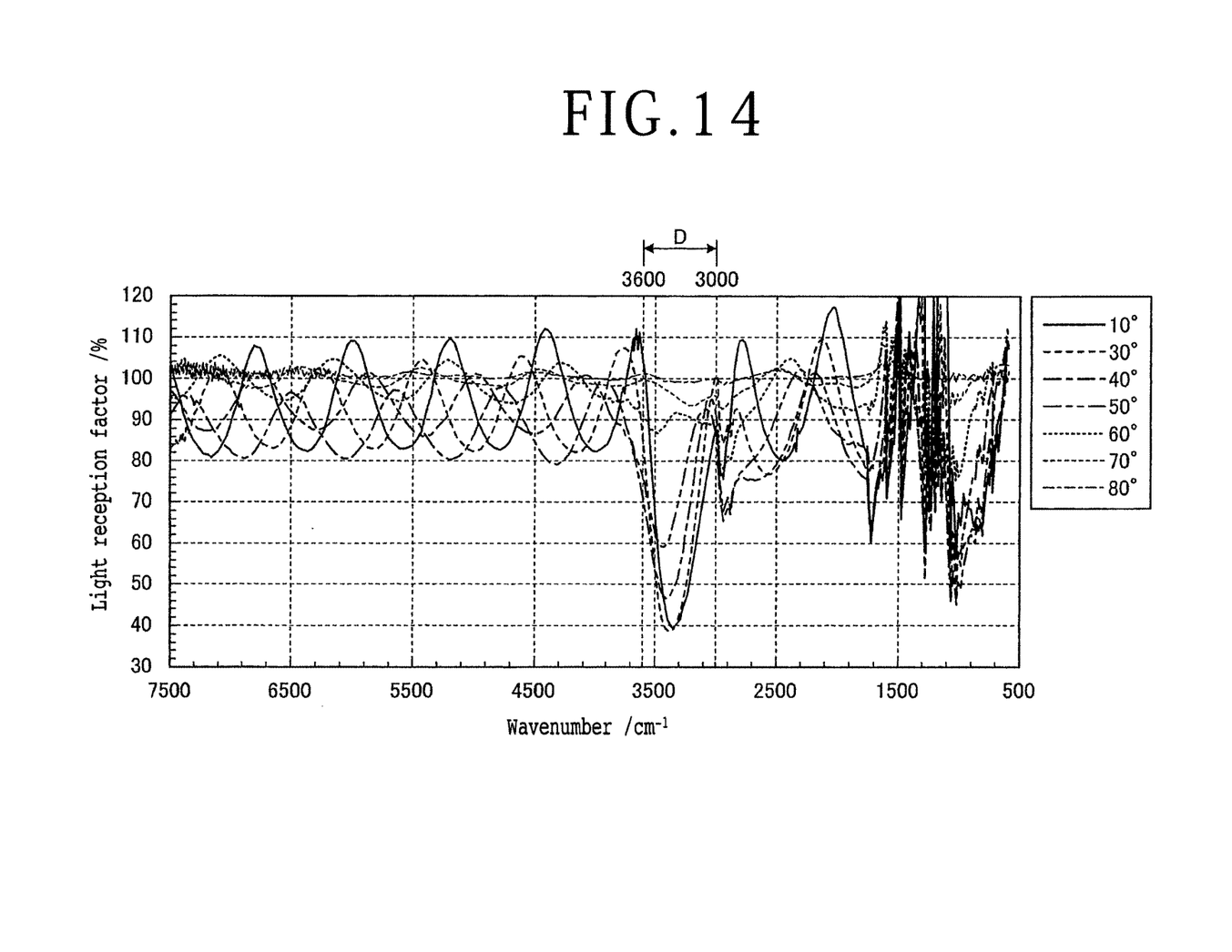
FIG. 14 is a diagram showing intensity of reflection from a water-soluble protective film on a workpiece in relation to intensity of reflection from a first region of a reference, in the case where workpieces formed with patterns are used as the reference and the workpiece and where an angle of infrared light at each wavelength is varied.

Now, a critical significance of the wavelength of the infrared light IR and the angle θ used in determining the threshold C in the threshold determining step ST13 in the protective film detecting method in the present invention will be described. In the following explanation, reference will be made of FIGS. 12 to 17. Note that FIG. 12 is a diagram showing the intensity of reflection from a water-soluble protective film on a workpiece relative to the intensity of reflection from the first region of a reference, in the case where workpieces not formed with any bump or pattern are used as the reference and the workpiece and where the angle of infrared light of each wavelength is varied. FIG. 13 is a diagram showing the intensity of reflection from a water-soluble protective film on a workpiece relative to the intensity of reflection from the first region of a reference, in the case where workpieces formed with bumps are used as the reference and the workpiece and where the angle of infrared light of each wavelength is varied. FIG. 14 is a diagram showing the intensity of reflection from a water-soluble protective film on a workpiece relative to the intensity of reflection from the first region of a reference, in the case where workpieces formed with patterns are used as the reference and the workpiece and where the angle of infrared light of each wavelength is varied. Note that the workpieces W in FIGS. 12 to 14 are coated with a water-soluble protective film P formed from a water-soluble resin containing PVA (polyvinyl alcohol) as a base material.

Figure 15:
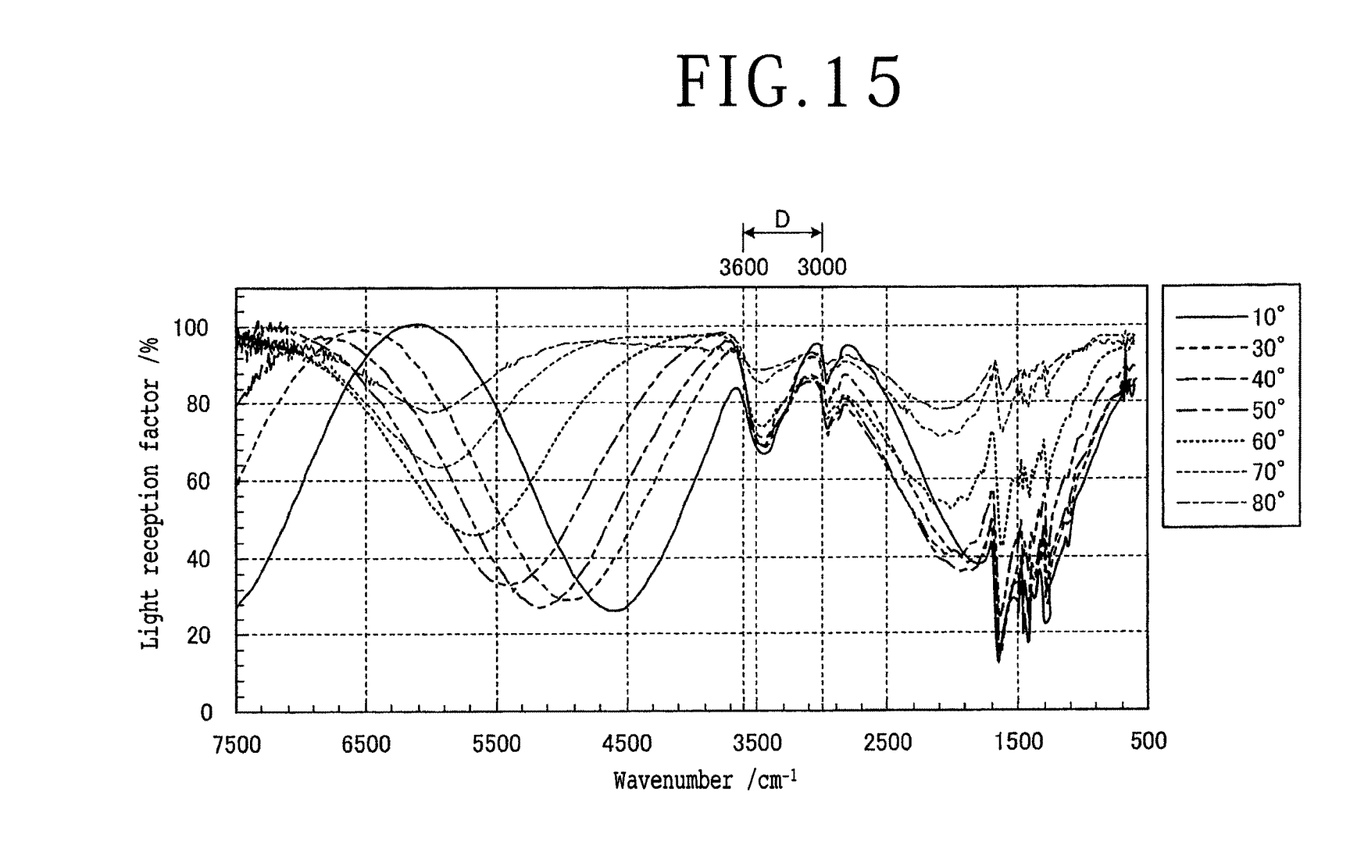
FIG. 15 is a diagram showing intensity of reflection from a water-soluble protective film on a workpiece in relation to intensity of reflection from a first region of a reference, in the case where workpieces not formed with any bump or pattern are used as the reference and the workpiece and where an angle of infrared light at each wavelength is varied.
Figure 16:
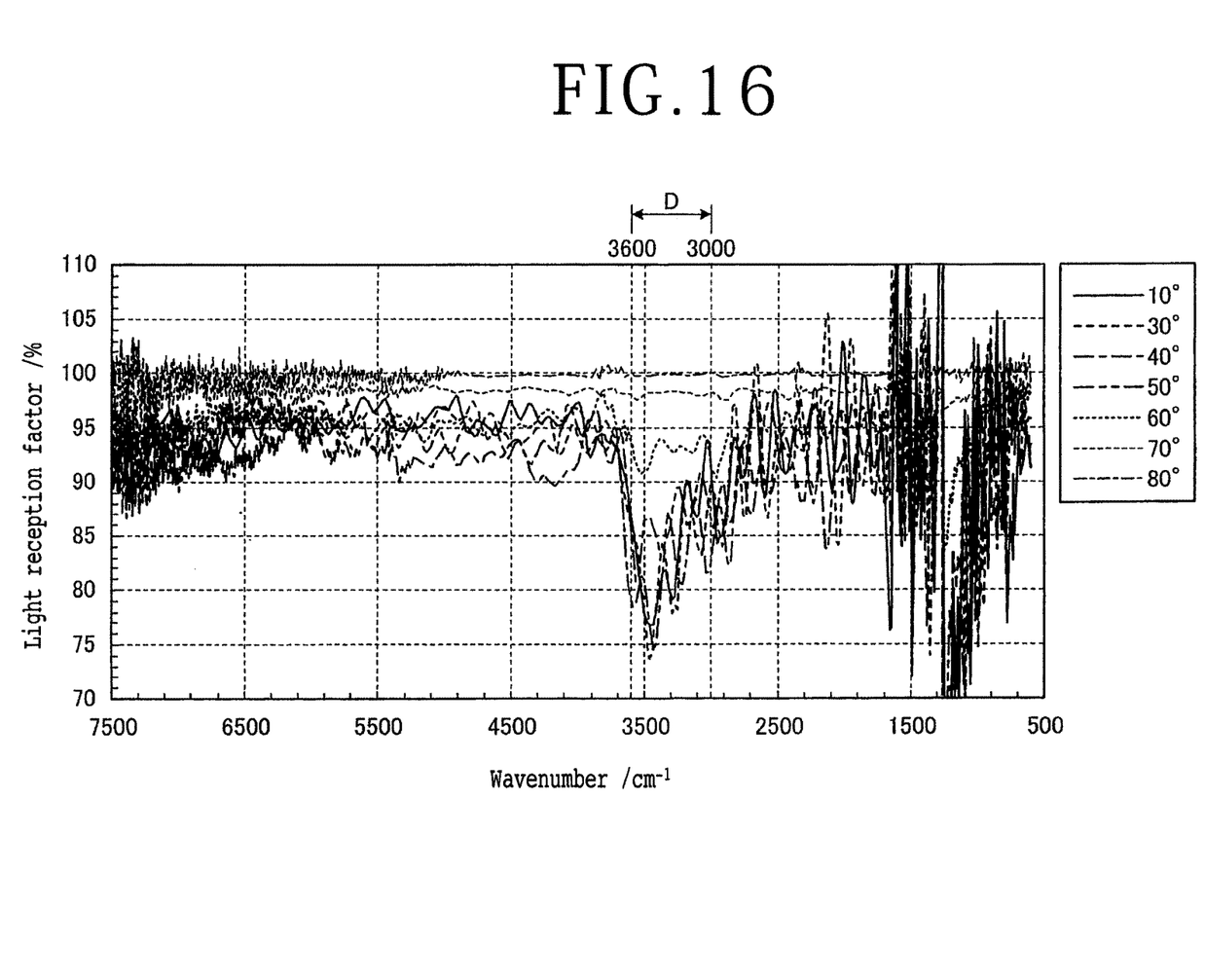
FIG. 16 is a diagram showing intensity of reflection from a water-soluble protective film on a workpiece in relation to intensity of reflection from a first region of a reference, in the case where workpieces formed with bumps are used as the reference and the workpiece and where an angle of infrared light at each wavelength is varied.
Figure 17:
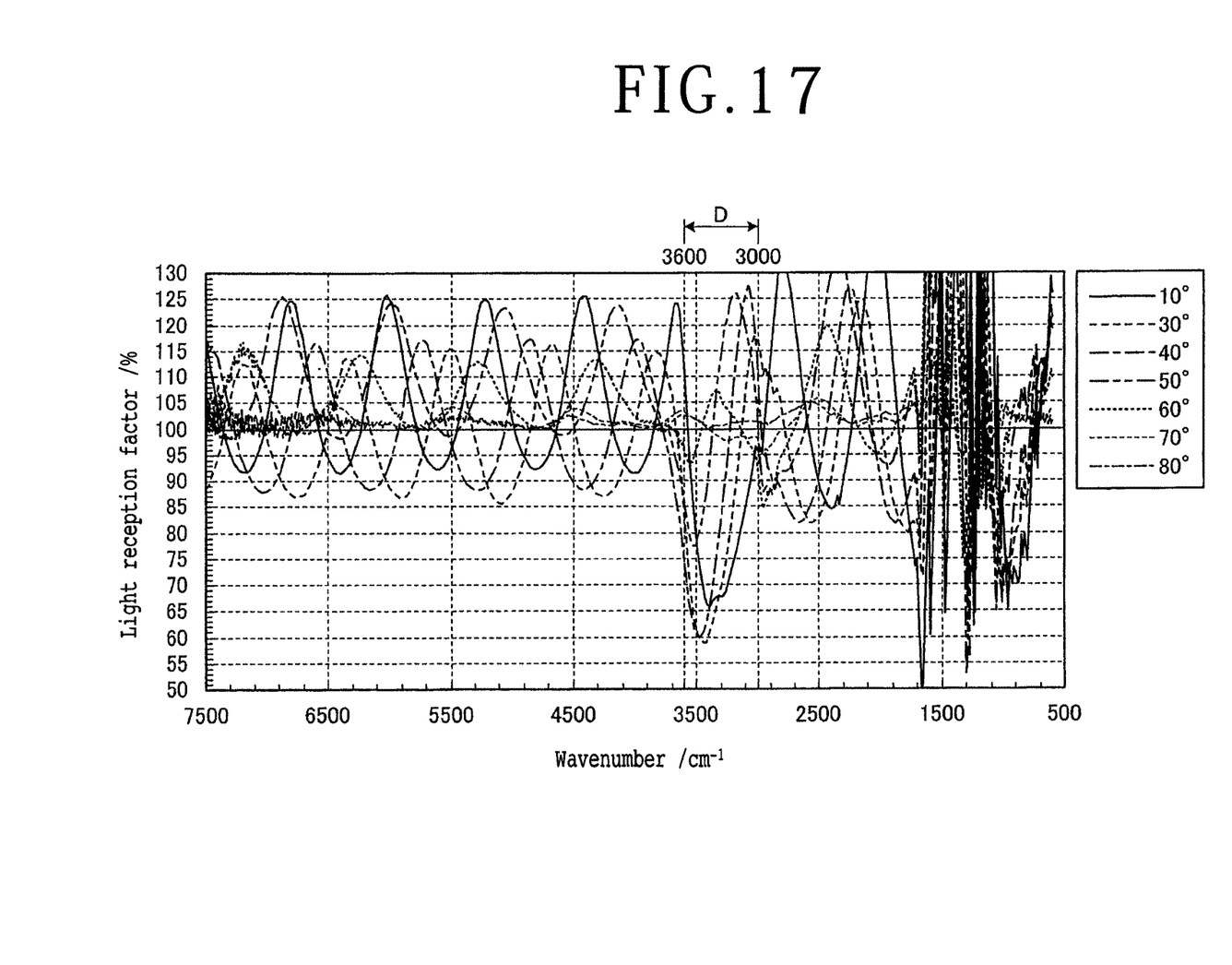
FIG. 17 is a diagram showing intensity of reflection from a water-soluble protective film on a workpiece in relation to intensity of reflection from a first region of a reference, in the case where workpieces formed with patterns are used as the reference and the workpiece and where an angle of infrared light at each wavelength is varied.

FIG. 15 is a diagram showing the intensity of reflection from a water-soluble protective film on a workpiece relative to the intensity of reflection from the first region of a reference, in the case where workpieces not formed with any bump or pattern are used as the reference and the workpiece and where the angle of infrared light of each wavelength is varied. FIG. 16 is a diagram showing the intensity of reflection from a water-soluble protective film on a workpiece relative to the intensity of reflection from the first region of a reference, in the case where workpieces formed with bumps are used as the reference and the workpiece and where the angle of infrared light of each wavelength is varied. FIG. 17 is a diagram showing the intensity of reflection from a water-soluble protective film on a workpiece relative to the intensity of reflection from the first region of a reference, in the case where workpieces formed with patterns are used as the reference and the workpiece and where the angle of infrared light of each wavelength is varied. Note that the workpieces in FIGS. 15 to 17 are coated with a water-soluble protective film P formed from a water-soluble resin containing PVP (polyvinyl pyrrolidone) as a base material.

In FIGS. 12 to 17, a thick solid line represents the case where the angle θ is 10°, a thick coarse broken line represents the case where the angle θ is 30°, a thick alternate long and short dashes line represents the case where the angle θ is 40°, a thick alternate long and two short dashes line represents the case where the angle θ is 50°, a thick dense broken line represents the case where the angle θ is 60°, a thin dense broken line represents the case where the angle θ is 70°, and a thin alternate long and short dashes line represents the case where the angle θ is 80°. In addition, the axis of abscissas in FIGS. 12 to 17 represents the wavenumber of infrared light IR, and the axis of ordinates represents the intensity of reflection from the water-soluble protective film P on the workpiece W when the intensity of reflection from the first region R1 of the reference R is taken as 100%.

According to FIGS. 12 to 17, it has been made clear that when infrared light IR having a wavelength range D in terms of wavenumber of 3000 cm$^{-1}$ to 3600 cm$^{-1}$ is used, the reflection intensity of the reflected light IRout from the workpiece W can be made sufficiently lower as compared to the reflection intensity of the reflected light IRout from the first region R1 of the reference R, whereby a difference is generated between the reflection intensities. The wavenumber of 3000 cm$^{-1}$ to 3600 cm$^{-1}$ corresponds to wavelengths that are absorbed by extension/contraction vibration of the OH group in PVA, or extension/contraction vibration of the NH group in PVP, or by hydrogen bonds of the group with water. Therefore, it has been verified that the use of infrared light IR having a wavelength range D in terms of wavenumber of 3000 cm$^{-1}$ to 3600 cm$^{-1}$ makes it possible to detect accurately the presence/absence of the water-soluble protective film P.

In addition, even where the infrared light IR having a wavelength range D in terms of wavenumber of 3000 cm$^{-1}$ to 3600 cm$^{-1}$ is used, if the angle θ is 0°, the configuration of each of the detection devices 10, 10-2 and 10-3 would be complicated, although a difference is generated between the reflection intensity of the reflected light IRout from the first region R1 of the reference R and the reflection intensity of the reflected light IRout from the workpiece W. For this reason, the angle θ formed between the incident light IRin and the reflected light IRout is desirably in the range of 0°<60°. Further, from FIGS. 13, 14, 16 and 17, it is clearly seen that even where the infrared light IR having a wavelength range D in terms of wavenumber of 3000 cm$^{-1}$ to 3600 cm$^{-1}$ is used, if the angle θ is 70° or 80°, little difference is generated between the reflection intensity of the reflected light IRout from the first region R1 of the reference R and the reflection intensity of the reflected light IRout from the workpiece W.

On the other hand, it has been verified according to FIGS. 13, 14, 16 and 17 that where the infrared light IR having a wavelength range D in terms of wavenumber of 3000 cm$^{-1}$ to 3600 cm$^{-1}$ is used and the angle θ is any of 10°, 30°, 40°, 50° and 60°, the reflection intensity of the reflected light IRout from the workpiece W can be made sufficiently low as compared to the reflection intensity of the reflected light IRout from the first region R1 of the reference R, whereby a difference is generated between the reflection intensities. Accordingly, it has been verified that by using the infrared light IR having a wavelength range D in terms of wavenumber of 3000 cm$^{-1}$ to 3600 cm$^{-1}$ and setting the angle θ to within the range of 0°<θ≤60°, it is possible to accurately detect the presence/absence of the water-soluble protective film P.

Note that the present invention is not limited to the aforementioned embodiments and modification. Various modifications are possible without departing from the scope of the gist of the present invention.

The present invention is not limited to the details of the above described preferred embodiments. The scope of the invention is defined by the appended claims and all changes and modifications as fall within the equivalence of the scope of the claims are therefore to be embraced by the invention.

What is claimed is:

1. A protective film detecting method for detecting whether or not a workpiece formed with a bump or a pattern on a surface thereof is coated with a water-soluble protective film, the method comprising:
    a reflection intensity acquiring step of irradiating with infrared light having a predetermined wavelength range a reference that has a first region preliminarily coated with the water-soluble protective film and a second region not coated with the water-soluble protective film, receiving reflected light, and acquiring an averaged intensity of reflection from the first region and an averaged intensity of reflection from the second region;
    a threshold determining step of determining a threshold value to be used as a reference for determining whether or not a surface of concern is coated with the water-soluble protective film, from the intensity of reflection from the first region and the intensity of reflection from the second region at a wavenumber of 3000 cm$^{-1}$ to 3600 cm$^{-1}$; and
    a detection step of sequentially irradiating a surface of the workpiece coated with the water-soluble protective film with the infrared light at a predetermined angle θ, receiving reflected light to acquire an intensity of reflection, comparing the thus acquired reflection intensity with the threshold value, and thereby detecting whether or not the surface of concern is coated with the water-soluble protective film,
    wherein the reference including the first region and the second region is different from the workpiece coated with the water-soluble protective film.

2. The method according to claim 1, wherein the predetermined angle θ is an angle formed between incident light and the reflected light, and is selected from the range of 0°<θ≤60°.

3. The method according to claim 1, wherein said reflective intensity acquiring step includes said irradiating with infrared light and said receiving of reflected light from a plurality of points in said first region and said irradiating with infrared light and said receiving of reflected light from a plurality of points in said second region.

4. The method according to claim 1, wherein said reflective intensity acquiring step is performed upon said reference that comprises a single reference workpiece that is divided into said first region and said second region.

5. The method according to claim 1, wherein said reflective intensity acquiring step is performed upon said reference that comprises two reference workpieces, wherein a first of said two reference workpieces consists only of said first region and a second of said two reference workpieces consists only of said second region.

6. The method according to claim 1, wherein the water-soluble protective film is composed of a water-soluble resin including polyvinyl alcohol as a base material.

7. The method according to claim 1, wherein the water-soluble protective film is composed of a water-soluble resin including polyvinyl pyrrolidone as a base material.

* * * * *